US011092588B2

(12) United States Patent
Bois et al.

(10) Patent No.: US 11,092,588 B2
(45) Date of Patent: Aug. 17, 2021

(54) MEASUREMENT CELL AND ASSOCIATED MEASUREMENT METHOD

(71) Applicant: Curis International, Duris-Au-Mont-d'Or (FR)

(72) Inventors: Axel-Pierre Bois, Curis-Au-Mont-d'Or (FR); Manh-Huyen Vu, Lyons (FR)

(73) Assignee: Curis International

(*) Notice: Subject to any disclaimer, the term of this patent is extended or adjusted under 35 U.S.C. 154(b) by 155 days.

(21) Appl. No.: 16/471,280

(22) PCT Filed: Dec. 12, 2017

(86) PCT No.: PCT/FR2017/053512
§ 371 (c)(1),
(2) Date: Jun. 19, 2019

(87) PCT Pub. No.: WO2018/115636
PCT Pub. Date: Jun. 28, 2018

(65) Prior Publication Data
US 2019/0317071 A1    Oct. 17, 2019

(30) Foreign Application Priority Data
Dec. 23, 2016  (FR) ....................................... 1663366

(51) Int. Cl.
*G01N 33/38*     (2006.01)
(52) U.S. Cl.
CPC .................................. *G01N 33/383* (2013.01)

(58) Field of Classification Search
CPC ............... G01N 33/383; G01N 15/082; G01N 15/0806; G01N 15/088
See application file for complete search history.

(56) References Cited

U.S. PATENT DOCUMENTS

| 2,217,278 A | 10/1940 | Kanter | |
| 5,226,310 A * | 7/1993 | Steiger | .................. E21B 49/006 73/38 |
| 5,265,461 A * | 11/1993 | Steiger | .................. G01N 29/07 73/38 |

(Continued)

FOREIGN PATENT DOCUMENTS

| FR | 2965925 | 4/2012 |
| WO | WO2012049620 | 4/2012 |

(Continued)

*Primary Examiner* — Peter J Macchiarolo
*Assistant Examiner* — Fatemeh Esfandiari Nia
(74) *Attorney, Agent, or Firm* — Forge IP, PLLC

(57) ABSTRACT

A measurement cell includes: an enclosure; a flexible membrane disposed in the enclosure so as to contain a hardenable material; and means for stiffening the membrane configured to assume two alternative states: a stiffness state, in which the stiffening means resist the expansion of the hardenable material during solidification; and a flexible state, in which the stiffening means exert a stress that is less than that exerted in the stiffness state allowing at least one physical, chemical or mechanical property of the hardenable material to be measured and the hardenable material to be extracted from the enclosure; the stiffening means being produced by a set of metal wires connected to a clasp configured to modify the stiffness exerted by the metal wires.

14 Claims, 2 Drawing Sheets

(56) References Cited

U.S. PATENT DOCUMENTS

| | | | | |
|---|---|---|---|---|
| 5,770,805 A | * | 6/1998 | Castel | G01F 1/20 |
| | | | | 73/861.04 |
| 6,591,690 B1 | * | 7/2003 | Crockford | G01N 3/10 |
| | | | | 73/760 |
| 7,040,156 B2 | * | 5/2006 | Crockford | G01L 5/0004 |
| | | | | 73/152.52 |
| 10,197,549 B2 | * | 2/2019 | Thomas | G01N 33/383 |
| 2013/0192382 A1 | | 8/2013 | Bois et al. | |
| 2013/0214771 A1 | * | 8/2013 | Tiernan | G01N 27/904 |
| | | | | 324/242 |

FOREIGN PATENT DOCUMENTS

| | | | | |
|---|---|---|---|---|
| WO | WO-2012049620 A1 | * | 4/2012 | G01N 33/383 |
| WO | WO-2016079558 A1 | * | 5/2016 | G01N 33/383 |

* cited by examiner

MEASUREMENT CELL AND ASSOCIATED MEASUREMENT METHOD

TECHNICAL FIELD

The invention relates to a cell for measuring at least one physical, chemical, or mechanical property of a hardenable material as well as to the associated measurement method.

The invention has a particularly advantageous application for measuring the mechanical properties of a cement so as to model the behavior of a cement casing or cement plug of an oil well.

BACKGROUND

The cementing of an oil well containment involves placing a cement casing in the ring between a containment and the wall of the hole, the hole potentially being formed by another containment or by the rock. This cement casing plays a critical role in the stability and insulation of oil wells.

Plugging a hydrocarbon well seeks to reestablish the natural integrity of the formations that have been penetrated by the borehole. To close a well, it is traditional to position cement plugs in line with certain geological formations in order to isolate the reservoirs.

The cement casing and plug are made by pumping a cement flow made from cement, water, and additives. This cement flow is in a liquid state when pumped. The cement particles are hydrated by dissolving and precipitating ions, leading the liquid flow into a solid state, characterized by the existence of a porous skeleton.

The cement casing and plug are exposed to various mechanical and thermal stresses during the lifespan of the well, caused by operations conducted inside the well (pressure tests, changing slurry, hot and cold stimulations, etc.) or phenomena arising directly underground (reservoir compaction, earthquakes, etc.), until it is abandoned, or even afterward.

These stresses may damage the material of the cement casing or plug, degrade its mechanical properties and permeability, and consequently, alter its contribution to the stability and leak-tightness of the well. Knowledge of the cement's behavior in well conditions and how it changes over time is essential to analyzing the operation of the well while it is in service, and also to ensure its leak-tightness for gas storage, particularly greenhouse gases (such as CO2).

The characteristics of the cement flow are determined based on a large number of parameters including the status of the earth near the cement casing or plug (temperature, pore pressure, state of stresses), the characteristics of the well (drilling fluid density, well stability, deviation, diameter of the borehole), the location of the cement casing or plug in the well, the pumping technique used, the stresses to which the cement casing or plug will be subjected, and the desired mechanical properties of the cement.

Therefore, independent of the intended application, it is important to accurately know the physical, chemical, or mechanical properties of the cement, as well as how they change during its hydration. To do so, it is known to carry out static tests by taking a sample of cement in a parallelepiped or cylindrical mold.

When the sample is solid, it is extracted from the mold, and the physical, chemical, or mechanical properties of that sample are tested.

For instance, for the mechanical properties, a traction or compression test is carried out along one or more axes.

However, this type of method is complex and takes a long time to carry out, because the sample goes through two devices: A first device to perform solidification, and a second device to take measurements. Furthermore, the sampling is preferably carried out under the downhole conditions of an oil well, e.g. at high temperature and pressure. When the sample is taken out of the mold, the temperature and pressure changes may degrade the physical, chemical, or mechanical properties of the sample. It follows that this type of method is unable to accurately measure the physical, chemical, or mechanical properties of hardened cement under the downhole conditions of an oil well.

Additionally, it is also desirable to know how the physical, chemical, or mechanical properties of cements change over the course of their hydration, in order to be able to calculate the state of stresses in the cement once hardened. This cannot be done with conventional static tests, because the samples must be testable before they harden.

To remedy these problems, there are multiple devices that propose measurement cells capable of both carrying out the solidification of the flow poured into a mold, and taking certain measurements without moving the sample.

For instance, the international patent application WO 2012/049620 describes an enclosure provided with an upper plate and lower plate, between which two half-cylinders capable of translational motion are installed. To take and characterize a cement sample, a flexible membrane is disposed inside the two half-cylinders.

The two half-cylinders are then moved around the membrane so as to form a cylindrical shell around the membrane. The cement is then inserted into the membrane. In this phase, during which the cement is liquid, the cement is retained by the solid enclosure around the membrane. The membrane can prevent the cement flow from adhering to the two half-cylinders, and makes it possible to thereafter apply a containment pressure without the fluid used to do so penetrating the cement pores.

During solidification, the sample is placed in the downhole temperature and pressure conditions of an oil well. To do so, pressure is applied to the cement placed inside the membrane by moving the lower and/or upper plate. Pressure is also applied within the enclosure by injecting a fluid around the two half-cylinders to simulate the pressure experienced by the cement under the downhole conditions of an oil well.

After a predetermined period of time, measurements are taken on that sample, while maintaining the downhole pressure and temperature conditions within the enclosure.

To do so, the two half-cylinders have two half-bores disposed substantially midway up the half-cylinders. When the two half-cylinders are moved around the membrane, the two half-bores cooperate to form a single circular bore. A sensor is positioned inside the bore until it reaches the membrane, and the sensor measures the changes in the sample's diameter. Other measurements are taken on the hardened cement after the two half-cylinders have been moved away from the membrane.

Finally, the fluid is purged from the enclosure, and the sensor and the two half-cylinders are moved away from the membrane. The sample and the membrane can then be extracted from the enclosure and another test can be performed by positioning a new flexible membrane in the enclosure.

This device is particularly effective because it makes it possible to take multiple measurements based on the standard protocol for triaxial tests. Its main drawback is that it requires the presence of moving parts, the two half-cylinders, which leads to problems with the overall dimensions and operational problems such as the risk that the half-cylinders will not completely close back up, causing a liquid cement leak, or will not open completely, thereby causing inaccurate measurements to be taken later. For this reason, radial deformation measurements must be taken using sensors in a radial position, and it is necessary, at the end of each test, to purge the enclosure of its oil. Consequently, preparing and dismantling a test takes several hours.

The technical problem of the invention is that of improving the measurement of at least one physical, chemical, or mechanical property of a hardenable material.

BRIEF DESCRIPTION OF THE INVENTION

To solve this technical problem, the invention proposes a new measurement cell comprising a membrane associated with a set of metal wires that ensure the stiffening of the membrane, which is required when solidifying the hardenable material.

To that end, according to a first aspect, the invention relates to a cell for measuring at least one physical, chemical, or mechanical property of a hardenable material, said cell comprising:
an enclosure;
a flexible membrane disposed in said enclosure in such a way as to contain said hardenable material; and
means for stiffening said membrane configured to assume two alternative states:
a stiffness state, in which said stiffening means resist the expansion of said hardenable material during solidification; and
a flexible state, in which said stiffening means exert a stress that is less than that exerted in the stiffness state, allowing at least one physical, chemical, or mechanical property of said hardenable material to be measured and said hardenable material to be extracted from said enclosure;
said stiffening means being produced by a set of metal wires connected to a clasp configured to modify the stiffness exerted by said metal wires.

The invention thereby makes it possible to limit the overall dimensions of the enclosure by incorporating the stiffening means into the membrane. Furthermore, the elimination of the two half-spheres makes it easier to integrate one or more sensors around the membrane. In particular, rather than using a sensor oriented in the radial direction of the sample, it is now possible to use a chain disposed around the membrane to measure the circumference variations of the sample.

Furthermore, after the measurements, the solidified sample can thereby be extracted from the enclosure without dragging the membrane along, because the stiffening means are in the flexible state. It is therefore no longer necessary to replace the membrane for each test. The result is that the fluid around the membrane can also be retained between two successive tests, which reduces the cycle time of each test by eliminating the steps of pumping and draining the fluid around the membrane.

According to one embodiment, said metal wires are disposed circumferentially at multiple heights of said membrane, the ends of each metal wire being fastened to said clasp. This embodiment makes it possible to apply radial counter-pressure to the sample during solidification. The pressure applied to the membrane is substantially equivalent to the pressure applied by the two half-cylinders of the prior art, while being simpler to implement and more compact.

According to one embodiment, the number n of metal wires meets the following condition:

$$\frac{L}{2r+e} \leq n \leq \frac{mL}{2r};$$

where L corresponds to the height of the cylindrical membrane (15), r to the radius or half-width of the metal wires, m to the number of wire layers, and e to the thickness of the membrane.

According to one embodiment, said enclosure comprises at least one radial motion sensor disposed circumferentially around said membrane between two metal wires. This embodiment makes it possible to dispose one or more circumferential sensors around the membrane, thereby limiting the overall dimensions and improving the accuracy of the measurements. Alternatively or additionally, an axial sensor can be used.

According to one embodiment, said membrane is made having an elastomer core. Preferably, said membrane is made having a core of polytetrafluoroethylene, such as the kind sold under the name Teflon®, or of fluorocarbon rubber, such as the kind sold under the name Viton®. This embodiment makes it possible to ensure the flexibility of the membrane while limiting the catching of the hardenable material onto the membrane.

Furthermore, Teflon® and Viton® are materials that can support the integration of the stiffening means, such as metal wires.

According to one embodiment, said enclosure is resistant to leaks of a pressurized fluid, so as to allow pressure to be applied around said membrane. This embodiment aims to apply pressure to a hardenable material during solidification, for example to simulate the downhole conditions of an oil well, or when conducting triaxial tests, for example to measure mechanical properties in containment.

According to one embodiment, said enclosure incorporates heating means so as to apply a temperature around said membrane. This embodiment aims to apply a temperature to a hardenable material during solidification, for example to simulate the downhole conditions of an oil well, or when conducting triaxial tests, for example to measure mechanical properties.

According to one embodiment, said membrane is disposed between a lower plate and an upper plate disposed at two openings in the enclosure, at least one plate being movable in translation so as to compress said hardenable material during solidification, when conducting tests and/or to extract said hardenable material from the enclosure.

This embodiment aims to apply an axial pressure to a hardenable material during solidification, for example to simulate the downhole conditions of an oil well. This embodiment also makes it possible to apply an axial stress when conducting triaxial tests, for example to measure mechanical properties.

According to a second aspect, the invention relates to a method for measuring at least one physical, chemical, or mechanical property of a hardenable material during solidification or afterward by means of a measurement cell according to the first aspect of the invention.

Said method comprises the following steps:
putting said stiffening means into said stiffness state;
pouring said hardenable material in liquid form into said membrane;

closing said enclosure;

solidifying said hardenable material;

when the required solidification state is achieved, putting said stiffening means into said flexible state;

measuring at least one physical, chemical, or mechanical property of said hardenable material; and extracting said hardenable material from said enclosure.

This second aspect of the invention thereby makes it possible to measure at least one physical, chemical, or mechanical property of a hardenable material without moving the material outside the enclosure.

According to one embodiment, when said measurement cell incorporates a leak-tight enclosure, said hardenable material is solidified by applying a pressure ramp within said enclosure.

According to one embodiment, when said measurement cell incorporates heating means, said hardenable material is solidified by applying a temperature ramp within said enclosure.

According to one embodiment, when said measurement cell incorporates a moving plate, said hardenable material is solidified by applying an axial stress ramp to said hardenable material.

According to one embodiment, the step of measuring at least one physical, chemical, or mechanical property of said hardenable material involves measuring the axial and radial deformations, and/or the pore pressure, and/or the velocity of the sonic compressional and shear waves, and/or the resistivity.

Based on some or all of these measurements, a large number of physical, chemical, or mechanical properties of the hardenable material can be obtained. For instance, based on the drained Young's modulus and Poisson's ratio, it is possible to find the shear modulus. Based on the shear-wave velocity, it is possible to determine the percolation threshold of the cement flow.

According to one embodiment, following the extraction of said hardenable material from said enclosure, said method comprises a step consisting of analyzing said hardenable material. This embodiment makes it possible to conduct other analyses on the hardenable material which cannot be conducted in the enclosure. For instance, a simple visual inspection can be conducted, or a more complex inspection such as X-ray tomography.

BRIEF DESCRIPTION OF THE FIGURES

The way to implement the invention as well as the advantages deriving therefrom will be clearly seen from the description of the following embodiment, supported by the appended figures in which.

WAYS TO IMPLEMENT THE INVENTION

Figure 1:
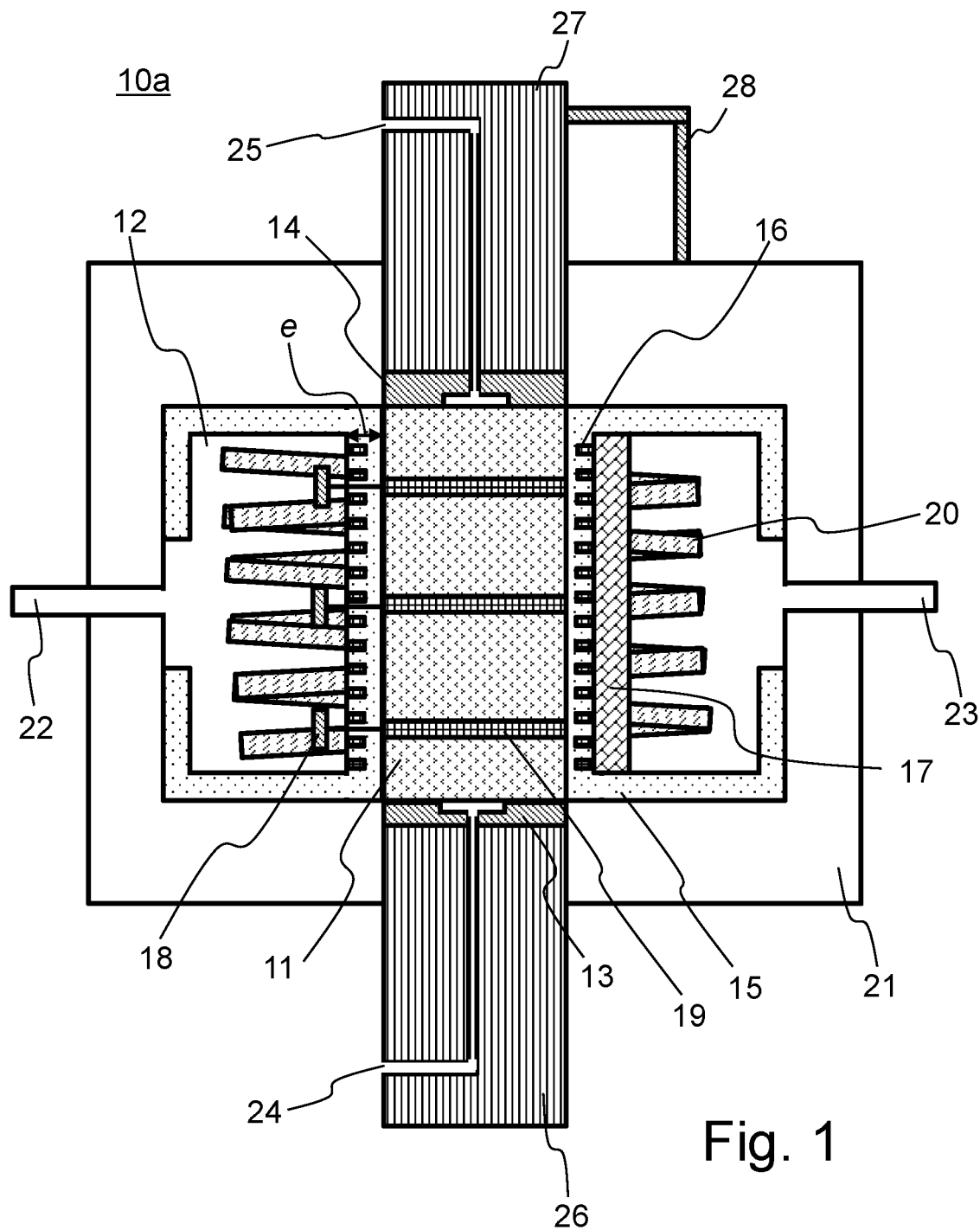
FIG. 1 is a cross sectional view of a measurement cell according to a first embodiment of the invention.

FIG. 1 illustrates a measurement cell 10a comprising an enclosure 12 intended for solidifying and measuring at least one physical, chemical, or mechanical property of a hardenable material 11.

The hardenable material 11 can be a cement flow, but other materials may be used without changing the invention, such as resins or glues. In the example of FIG. 1, the hardenable material 11 is formed into the shape of a cylinder, but other shapes may be implemented without changing the invention.

The enclosure 12 has the shape of a cylindrical chamber built into a metal frame 21, such as one made of steel or aluminum. The frame 21 features an upper opening and a lower opening. The openings are blocked by moving plates 13, 14 driven by one or two pistons 26, 27. The hardenable material 11 is disposed between the two plates 13, 14. A fluid channel 24 passes through the lower piston 26 and the lower plate 13 to empty into a chamber of the lower plate 13 so as to apply pore pressure from the lower end of the hardenable material 11.

Likewise, a fluid channel 25 passes through the upper piston 27 and the upper plate 14 to empty into a chamber of the upper plate 14 so as to apply pore pressure from the upper end of the hardenable material 11. The hardenable material 11 is also radially stressed by a deformable membrane 15 associated with a set of metal wires 16 radially disposed around the hardenable material 11. The membrane 15 is preferably made of an elastomer, such as Teflon® or Viton®.

As shown in FIG. 1, the metal wires 16 may be sunk into the external edge of the membrane 15 around the hardenable material 11. The metal wires 16 are disposed at multiple heights of the membrane 15.

In one variant, the metal wires 16 may surround the membrane 15. In one variant, the metal wires 16 may form a metal grid. In one variant, the metal wires 16 may extend longitudinally relative to the hardenable material 11.

The ends of the metal wires 16 are fastened to the two sides of a remotely controlled clasp 17. Said clasp 17 may assume two positions: A closed position and an open position.

In the closed position, tension may be exerted on the metal wires 16 so as to stiffen the membrane 15 and radially contain the hardenable material 11. In the open position, the metal wires 16 are in a flexible state.

The dimensions and number of the wires 16 are designed to avoid the membrane 15 being extruded if the pressure inside is greater than the pressure outside the membrane 15. To do so, it is possible to model the stresses experienced by the wires 16 for a membrane 15 with internal and external diameters of Ri and Ro, respectively. The part of the membrane 15 in contact with the hardenable material 11, is surrounded by a layer of n steel wires whose circular cross-section has the diameter r. Other cross-sections may be used without changing the invention, such as square or rectangular cross-sections. The ability to use multiple layers of wires is also possible. The external and internal pressures of the membrane 15 are respectively denoted po and pi.

The temperature variation within the membrane 15 is considered homogeneous. The stresses in the membrane 15 are first calculated assuming there are no steel wires 16. The tangential stress borne by the membrane 15, when there are no steel wires 16, is given by:

$$\sigma_\theta = A + \frac{B}{r}$$

$$A = \frac{p_o R_o^2 - p_i R_i^2}{R_o^2 - R_i^2}$$

$$B = \frac{(p_o - p_i) \cdot R_o^2 R_i^2}{R_o^2 - R_i^2}$$

Next, the stress in the steel wires 16 is obtained by considering the balance of force between the membrane 15 with the calculated stresses and the steel wires 16. Considering the system of the membrane 15 and the steel wires 16, the force generated by the tangential stress of the membrane 15 is calculated by the following expression:

$$F = L \cdot \int_{R_i}^{R_o} \left(A + \frac{B}{r}\right) \cdot dr$$

where L corresponds to the length of the sample.

This expression may be integrated as follows:

$$F = L \cdot (R_o - R_i) \cdot \left(A + \frac{B}{R_o R_i}\right)$$

By replacing the expression of A and B in the expression of F, the result is:

$$F = \frac{L}{R_o + R_i} \cdot [p_o R_o^2 - p_i R_i^2 + (p_o - p_i) R_o R_i]$$

The distribution of this force across m layers of n steel wires 16 makes it possible to obtain the following stress in the wires 16:

$$\sigma_w = \frac{F}{2nm \cdot \pi r^2}$$

Thus, when the internal pressure pi is much higher than the external pressure po, the tangential stress F is negative and the wires 16 are in tension. When the internal pressure pi is slightly higher than the external pressure po, the wires 16 are in compression.

To ensure that the cell 10a operates correctly, the number of wires 16 must meet the following condition:

$$\frac{L}{2r + e} \leq n \leq \frac{mL}{2r}$$

In the example of FIG. 1, the membrane 15 has a thickness e of between 2 and 4 mm and the metal wires 16 have a diameter of between 0.5 and 1 mm. The hardenable material 11 has a length of between 65 and 80 mm and a diameter of between 30 et 40 mm. The number of wires 16 is preferably between 35 and 45 for a single layer.

This system of wires 16 has notches in order to allow the positioning of sensors 18 for measuring radial deformations. Thus, three radial motion sensors 18 are installed at three different heights of the hardenable material 11 using three non-deformable chains 19 that surround the membrane 15. An axial motion sensor 28 of the upper plate 14 is also disposed above the frame 21. In one variant, the cell 10a may also incorporate sensors to measure the compressional and shear wave velocities in the hardenable material 11, the resistivity of the material 11, or any other physical/chemical/mechanical parameter of the material 11.

To reproduce the pressure conditions, the enclosure 12 is hermetically sealed through the use of a membrane 15 that at least partially follows the internal and external walls of the enclosure 12.

Thus, when pressure is applied within the enclosure 12, the membrane 15 is held against the material 11 by the part of the membrane 15 in contact with the outer edge of the enclosure 12. The pressure in the enclosure 12 is generated by a containment fluid injected and controlled by two conduits 22, 23 that pass through a central part of the frame 21.

To reproduce the temperature conditions, a heating and/or cooling coil 20 is installed in the cell 12, immersed in the containment fluid. The purpose of this system is to control and/or effectively set the temperature of the material 11. Preferably, the input and output of the heating/cooling system are placed in the middle of the frame 21.

Alternatively or additionally, an external heating shell may also be disposed around the frame 21.

One example of measuring the physical, chemical, or mechanical properties of a cement plug is described below, using cell 10a of FIG. 1.

In a first step, the lower plate 13 is positioned at the lower end of the enclosure 12. The membrane 15 is stiffened by closing the clasp 17. A liquid cement flow is injected into the membrane 15 through the upper opening in the enclosure 12 to the level of the upper opening, thereby making it possible to obtain a sample with the shape of a solid cylinder. In one variant, a cylinder may be inserted into the center of the cement flow so as to form a sample having the shape of a hollow cylinder. To finish this step of preparing the test, the upper plate 14 is put in place, so as to close the cement's containment chamber.

In a second step, the upper piston 27 is activated to move the upper plate 14 so as to apply pressure in the cement, said pressure being absorbed by the metal wires because the clasp is in the closed position. Likewise, a variation in the containment pressure is applied within the enclosure 12 over time by means of the conduits 22, 23, and a predetermined temperature variation is applied within the enclosure 12 over time by means of the heating and/or cooling means 20.

The cement's mechanical properties can be measured when the cement is solidifying and/or after solidification. Thus, in a third step, to take measurements after a required solidification level, the membrane 15 is relaxed by opening the clasp 17.

A triaxial test is then carried out, checking the axial stress, containment pressure, temperature, pore pressure, and physical/chemical composition of the pore fluid. The axial and radial deformations are measured by the sensors 18, 28 and the pore pressure is obtained by the channels 24, 25. Other measures may be taken to obtain the velocity of the sonic compressional and shear waves, measure the resistivity, or measure any other physical/chemical/mechanical parameter of the cement or its components.

In a fourth step, after the axial stress, containment pressure, pore pressure, and sample temperature have been adjusted to the ambient values, the sample is extracted from the enclosure 12 by removing the upper piston 27 and moving the sample by pushing the lower piston 26. The sample is thereby recovered, and a visual inspection or X-ray tomography inspection may be conducted outside the enclosure 12 while another measurement can be taken by putting the cell 10a back in the first step.

Figure 2:
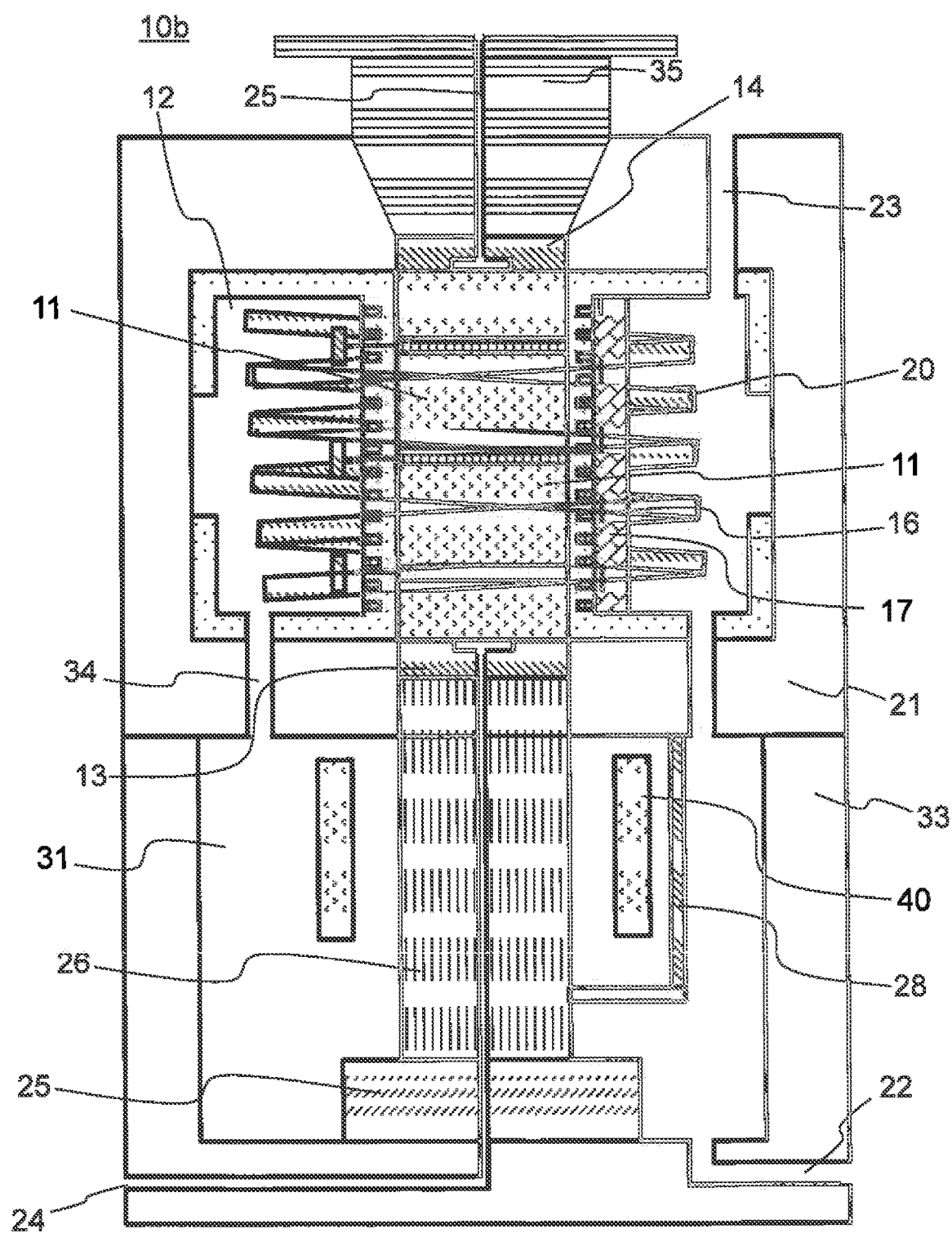
FIG. 2 is a cross sectional view of a measurement cell according to a second embodiment of the invention.

FIG. 2 shows a cell 10b operating by the same principle as the cell 10a of FIG. 1. Said cell 10b incorporates a loading frame. To do so, the cell 10b is made up of two chambers:

An enclosure 12 intended to contain a hardenable material 11, and a loading chamber 31.

The hardenable material 11 is solidified and measured in the enclosure 12 while the hydraulic cylinders 25, 26 and the axial motion sensor 28 are installed in the loading chamber 31.

The loading chamber 31 is hydraulically connected to the enclosure 12 by recesses 34 communicating between the frame 21 forming the enclosure 12 and the frame 33 forming the loading chamber 31 so as to balance the pressure between the two chambers 21, 31.

This embodiment makes it possible to increase the accuracy of the axial motion sensor 28, because it operates at the same pressure as the enclosure 12. Preferably, the two chambers 12, 31 are fastened to one another by bolts.

The loading chamber 31 comprises a cylinder 25 with a large force capacity, making it possible to axially load the material 11 during solidification or measurement, and a cylinder 26 with a large displacement capacity, making it possible to extract the material 11 from the enclosure 12. The upper cylinder is replaced with a cap 35 fastened to the frame 21, after inserting the hardenable material 11 into the enclosure 12.

The containment fluid intake 22 is placed in the loading chamber 31 while the containment fluid outlet 23 is built into the enclosure 12. The pore pressure in the hardenable material 11 is controlled by a pressure generator through two channels 24, 25. A first channel 24 is built into the frame 33 of the loading chamber 31, the two cylinders 25, 26, and the lower plate 13, while the second channel is formed in the cap 35 and the upper plate 14.

To reproduce the temperature conditions, a heating and/or cooling coil 20 is installed in the cell 12, immersed in the containment fluid. Furthermore, the loading chamber 31 has heating means 40 configured by maintaining a temperature gradient within the sample.

Alternatively or additionally, a heating plate may be disposed between the upper cap 35 so as to also improve the temperature gradient within the sample.

The axial motion measurement system is formed by a high-precision motion sensor 28 welded to a "magnetic skate". The magnetic skate is activated when the stroke of the motion sensor 28 is reached.

During the tests, the magnetic skate is not activated, and the motion sensor 28 measures the movement of the cylinder 26. When the hardenable material 11 is removed, the magnetic skate is activated, and the cylinder 26 can move upward freely without damaging the axial motion sensor 28.

The invention makes it possible to measure the physical, chemical, or mechanical properties of a hardenable material 11 in its usage conditions during the hydration phase until it sets, or even afterward, without returning to the atmospheric pressure and ambient temperature conditions.

The cell 10b corresponds to a triaxial cell, because the measurements are taken under axial stress variations by imposing a containment pressure around the hardenable material 11. These measurements make it possible to obtain the static deformation and rupture properties under triaxial conditions during or after setting, as well as the hydraulic conductivity properties.

The invention claimed is:

1. A cell for measuring at least one physical, chemical, or mechanical property of a hardenable material, said cell comprising:
   an enclosure;
   a flexible membrane disposed in said enclosure in such a way as to contain said hardenable material; and
   means for stiffening said membrane configured to assume two alternative states:
      a stiffness state, in which said stiffening means resist the expansion of said hardenable material during solidification; and
      a flexible state, in which said stiffening means exert a stress that is less than that exerted in the stiffness state, allowing at least one physical, chemical, or mechanical property of said hardenable material to be measured and said hardenable material to be extracted from said enclosure;
   wherein said stiffening means are produced by a set of metal wires connected to a clasp configured to modify the stiffness exerted by said metal wires;
   wherein the number n of metal wires meets the following condition:

$$\frac{L}{2r+e} \leq n \leq \frac{mL}{2r};$$

where L corresponding to the height of a cylindrical membrane, r to the radius or half-width of the metal wires, m to the number of wire layers, and e to the thickness of the membrane.

2. The measurement cell according to claim 1, wherein said metal wires are disposed circumferentially at multiple heights of said membrane, the ends of each metal wire being fastened to said clasp.

3. The measurement cell according to claim 2, wherein said enclosure comprises at least one radial motion sensor disposed circumferentially around said membrane between two metal wires.

4. The measurement cell according to claim 1, wherein said membrane has an elastomer core.

5. The measurement cell according to claim 4, wherein said membrane is made having a core of polytetrafluoroethylene or of fluorocarbon rubber.

6. The measurement cell according to claim 1, wherein said enclosure is resistant to leaks of a pressurized fluid, so as to allow pressure to be applied around said membrane.

7. The measurement cell according to claim 1, wherein said enclosure incorporates heating means so as to apply a temperature around said membrane.

8. The measurement cell according to claim 1, wherein said membrane is disposed between a lower plate and an upper plate disposed at two openings in the enclosure, at least one plate being movable in translation so as to compress said hardenable material during solidification, when conducting tests and/or to extract said hardenable material from the enclosure.

9. A method for measuring at least one physical, chemical, or mechanical property of a hardenable material during solidification or afterward by means of a measurement cell according to claim 1, said method comprising the steps of:
   putting said stiffening means into said stiffness state;
   pouring said hardenable material in liquid form into said membrane;
   closing said enclosure;
   solidifying said hardenable material;
   when the required solidification state is achieved, putting said stiffening means into said flexible state;
   measuring at least one physical, chemical, or mechanical property of said hardenable material; and
   extracting said hardenable material from said enclosure.

10. The measurement method according to claim 9, wherein, when said measurement cell incorporates a leak-tight enclosure resistant to leaks of a pressurized fluid so as to allow pressure to be applied around said membrane, said hardenable material is solidified by applying a pressure ramp within said enclosure.

11. The measurement method according to claim 9, wherein, when said measurement cell incorporates heating means so as to apply a temperature around said membrane, said hardenable material is solidified by applying a temperature ramp within said enclosure.

12. A measurement method according to claim 9, wherein, when said measurement cell incorporates a membrane disposed between a lower plate and an upper plate disposed at two openings in the enclosure, at least one plate being movable in translation so as to compress said hardenable material during solidification when conducting tests and/or to extract said hardenable material from the enclosure, said hardenable material is solidified by applying an axial stress ramp on said hardenable material.

13. The method according to claim 9, wherein, the step of measuring at least one physical, chemical, or mechanical property of said hardenable material involves measuring the axial and radial deformations, and/or the pore pressure, and/or the velocity of the sonic compressional and shear waves, and/or the resistivity.

14. The method according to claim 9, wherein, following the extraction of said hardenable material from said enclosure, said method comprises a step consisting of analyzing said hardenable material.

\* \* \* \* \*